United States Patent
Samuilov

(10) Patent No.: US 9,086,363 B2
(45) Date of Patent: Jul. 21, 2015

(54) CARBON NANOTUBE DEWPOINT AND ICE CONDITION SENSOR

(75) Inventor: Vladimir Samuilov, Stony Brook, NY (US)

(73) Assignee: THE RESEARCH FOUNDATION OF STATE UNIVERSITY OF NEW YORK., Albany, NY (US)

( * ) Notice: Subject to any disclaimer, the term of this patent is extended or adjusted under 35 U.S.C. 154(b) by 195 days.

(21) Appl. No.: 13/062,658

(22) PCT Filed: Sep. 8, 2009

(86) PCT No.: PCT/US2009/056273
§ 371 (c)(1),
(2), (4) Date: Mar. 7, 2011

(87) PCT Pub. No.: WO2010/028392
PCT Pub. Date: Mar. 11, 2010

(65) Prior Publication Data
US 2011/0167894 A1    Jul. 14, 2011

Related U.S. Application Data

(60) Provisional application No. 61/094,444, filed on Sep. 5, 2008.

(51) Int. Cl.
*G01N 25/00* (2006.01)
*G01N 27/12* (2006.01)
*G01N 5/02* (2006.01)

(52) U.S. Cl.
CPC ............ *G01N 27/121* (2013.01); *G01N 27/127* (2013.01)

(58) Field of Classification Search
CPC ..... G01N 27/127; G01N 2/121; G01N 25/56; G01N 27/048; G01N 2291/0256; G01N 2291/02845; G01N 25/66; G01N 25/68; G01N 27/126; G01N 25/70; G01N 2291/0251; G01N 2291/0257; B82Y 30/00; G08B 19/02; B64D 15/20; Y10S 977/953; Y10S 977/957
USPC ............... 73/29.01, 29.05, 335.05, 29.02, 73; 374/16, 141, 28, 185, 45
See application file for complete search history.

(56) References Cited

U.S. PATENT DOCUMENTS 5,364,185 A     11/1994   VanZandt et al.
6,276,202 B1 *   8/2001   Latarius ..................... 73/335.05
(Continued)

FOREIGN PATENT DOCUMENTS

JP      2005070038      3/2005
KR   1020060070672     6/2006
(Continued)

OTHER PUBLICATIONS

McMillan, G.K.; Considine, D.M. (1999). Process/Industrial Instruments and Controls Handbook (5th Edition). (pp. 7.15). McGraw-Hill.*
(Continued)

*Primary Examiner* — Daniel S Larkin
*Assistant Examiner* — Jamar Ray
(74) *Attorney, Agent, or Firm* — Scully, Scott, Murphy & Presser, P.C.

(57) ABSTRACT

Disclosed is a dewpoint and icing condition detection apparatus that includes a sensor, a signal conditioner and a data acquisition device. The sensor is a carbon nanotube sensor having a resistance that varies in proportion to a change in humidity of a gas flow across the sensor.

5 Claims, 4 Drawing Sheets

(56) References Cited

U.S. PATENT DOCUMENTS

| | | |
|---|---|---|
| 6,865,940 B2 | 3/2005 | Poole |
| 2002/0040598 A1* | 4/2002 | Sugaya et al. ............. 73/335.02 |
| 2004/0135684 A1* | 7/2004 | Steinthal et al. ............. 340/522 |
| 2005/0036905 A1* | 2/2005 | Gokturk ......................... 422/55 |
| 2010/0089772 A1* | 4/2010 | Deshusses et al. ............ 205/781 |

FOREIGN PATENT DOCUMENTS

| | | |
|---|---|---|
| KR | 1020070112657 | 11/2007 |
| WO | WO 2013/043148 | 3/2013 |

OTHER PUBLICATIONS

Ma, Xingpa, et al., Gas Sensing Behavior of Nano-Structured Polypyrrole Prepared by "Carbon Nanotubes Seeding" Approach, Journal of Nanoparticle Research, Feb. 2008, vol. 10 No. 2, pp. 289-296.

PCT/ISA/237 Written Opinion issued on PCT/US2009/056273 (4 pp.).

PCT/ISA/210 Search Report issued on PCT/US2009/056273 (3 pp.).

Thomas, Dan, Aerosonde Robotic Aircraft, Barrow Aug. 2000 Operation: Icing Sensor Data Report, Sep. 21, 2000.

LPDT User's Manual, LDO.01.D/2000 Rev.0 Jun. 1, 1999, Xentaur Corporation.

* cited by examiner

CARBON NANOTUBE DEWPOINT AND ICE CONDITION SENSOR

PRIORITY

This application claims priority to U.S. Provisional Application No. 61/094,444, filed Sep. 5, 2008, the contents of which are incorporated herein by reference.

BACKGROUND OF THE INVENTION

1. Field of the Invention

The present invention generally relates to moisture sensors and, in particular, to carbon nanotube sensors for repeated detection of relative humidity, and methods for operation thereof.

2. Brief Description of the Background Art

Conventional moisture sensing systems include a Loop Powered Dewpoint Transmitter (LPDT), such as the HTF™ $Al_2O_3$ sensor provided by Xentaur Corporation. The LPDT system allows a user to view dewpoint by monitoring the operation of a sensor constructed as a capacitor having a dielectric that consists of porous aluminum oxide, as well as monitoring the gas that enters pores of the aluminum oxide. The capacitor plates, i.e. electrodes, are an aluminum substrate and a porous gold layer deposited on top of the aluminum oxide, and the electrode having the porous gold layer allows transfer of gases into or out of the aluminum oxide pores. The capacitance due to the aluminum oxide is constant, while the capacitance due to the gas will vary according to the gas content and pressure. Since the dielectric constant of water is orders of magnitude larger than the dielectric constant of any gas being measured, the quantity of water vapor present in the pores will change the capacitance of the sensor to a much greater extent than other variables.

Dewpoint from the LPDT system can be obtained from Equation (1):

$$D = \frac{(I-4) \times (H-L)}{16} + L, \quad (1)$$

where I is the current drawn by the LPDT, H is a value of the high end of an analog output range, L is a value of a low end of the analog output range, and D is the measured dewpoint. However, use of the LPDT sensor will often cause the pore volume to change due to contaminant clogging, residual oxidation, metal migration, etc. Thus, recalibration of the sensor is needed, based on a capacitance at a wet end of the dewpoint-capacitance curve, such as shown in FIG. 1.

Another conventional system is described in U.S. Pat. No. 6,865,940 to Poole, which is incorporated herein by reference. Poole utilizes an aluminum oxide moisture sensor that requires several hours to reach equilibrium levels that vary by application process.

Conventional ice sensors include a control unit and a sensor probe, which contains a control unit monitored with two parallel, redundant optical beams with corresponding detectors. See, e.g. Aerosonde Robotic Aircraft Report dated Sep. 21, 2000, *Barrow August 2000 Operation: Icing Sensor Data Report* by Dan Thomas. The control unit will monitor intensity of the beams to detect ice buildup. The parallel beams are used to protect against false readings of ice accretion. The sensor probe also contains temperature sensors used by the control unit logic to verify that the air temperature is below a threshold temperature, at which temperature icing can occur. However, ice layers accumulate very quickly, making early detection of ice formation imperative in applications such aircraft safety.

SUMMARY OF THE INVENTION

The present invention provides a sensor that is of reduced size, can be manufactured at lower, functions using a simplified process, and is capable of measuring a dewpoint of −80° C. to +20° C.

In addition, the present invention detects icing on a molecular level, based on humidity in the air via monitoring of resistance change in a nanosensor, based on an absorbing layer of the CNTs. The absorption of the water vapor at temperatures close to freezing conditions leads to a specific non-monotonous temperature dependence of the resistance of a Carbon NanoTube (CNT) sensor.

The present invention overcomes shortcomings of conventional systems by use of a CNT sensor that reduces measurement error from residual moisture that minimizes recalibration time and simplifies the recalibration process, that provides a faster response time, and that allows for detection of an icing condition prior to ice layer build-up.

BRIEF DESCRIPTION OF THE DRAWINGS

The above and other objects, features and advantages of certain exemplary embodiments of the present invention will be more apparent from the following detailed description taken in conjunction with the accompanying drawings, in which.

DETAILED DESCRIPTION OF THE PREFERRED EMBODIMENTS

The following detailed description of preferred embodiments of the present invention is made with reference to the accompanying drawings. In describing the invention, an explanation of related functions or constructions known in the art are omitted for the sake of clearness in understanding the concept of the invention, and to avoid obscuring the invention with unnecessary detail.

In the present invention, chemically activated CNTs are utilized to form a CNT film for the sensor body. In a preferred embodiment, 10-20 nm multi-wall CNTs are used, having a length of 2-5 micrometers. Chemical activation is preferably accomplished by dispersing of multi-wall CNT sample in an acid mixture of 98% wt $H_2SO_4$ and $HNO_3$ in a 3:1 volume ratio. The mixture is ultra-sonicated for three hours in a water bath, and stirred for five hours at 55° C. The temperature is then decreased from approximately 55° C. to 35° C. and the mixture stirred for two days. The mixture is filtered with a 0.1 micron Cellulose Easter filter, and the filtered oxidized mixture is extensively washed with distilled water until a neutral pH is obtained. The mixture is then oven dried for one day to obtain a powder, which is lifted by dissolving the filtered polymer background in a solvent. This procedure oxidizes the CNTs to introduce dangling bonds on an outer surface of the multi-wall CNTs, introducing a charge on the surfaces.

Thick films and free-standing membranes are assembled by using the oxidized CNTs to form free-standing films of micrometer thickness that assemble on the Cellulose Easter filter surface during the step of filtering the oxidized solution of CNT in water. The CNT films lifted in acetone from the filter surface are placed on a dielectric surface and silver (Ag) paste used to create a pair of 1×3 mm electrodes separated on the surface of a 3×8 mm$^2$ sensor element.

Figure 1:
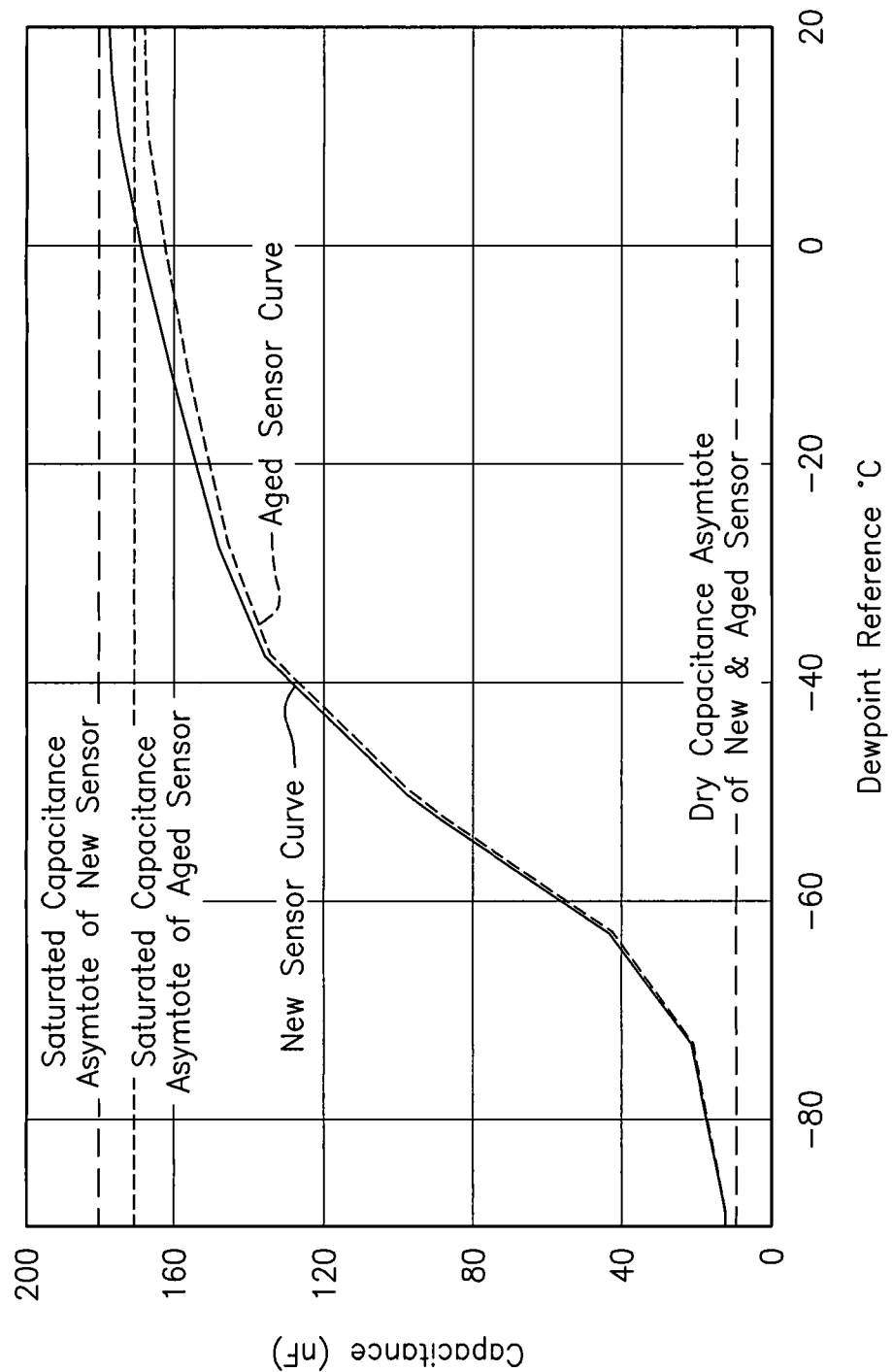
FIG. 1 shows a relationship of a dewpoint reference and capacitance measured by a conventional system.
Figure 2:
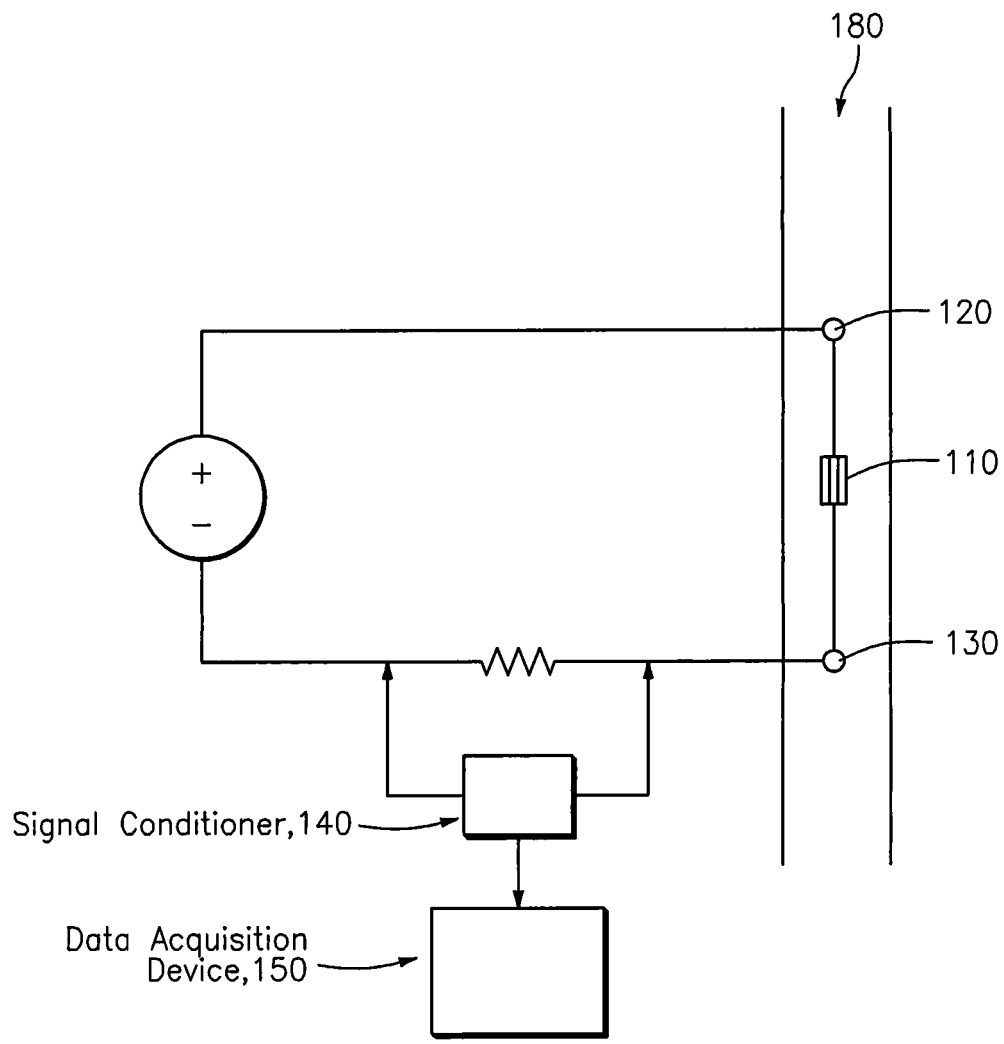
FIG. 2 is block diagram of the CNT sensor and system for use thereof of the present invention.

As shown in FIG. 2, a sensor 110 formed from the activated CNTs is placed in a vapor flow 180, which can include non-hydrocarbon gas streams, in hydrocarbon gas streams, and in hydrocarbon liquid streams, to measure moisture content and dewpoint thereof.

Figure 3:
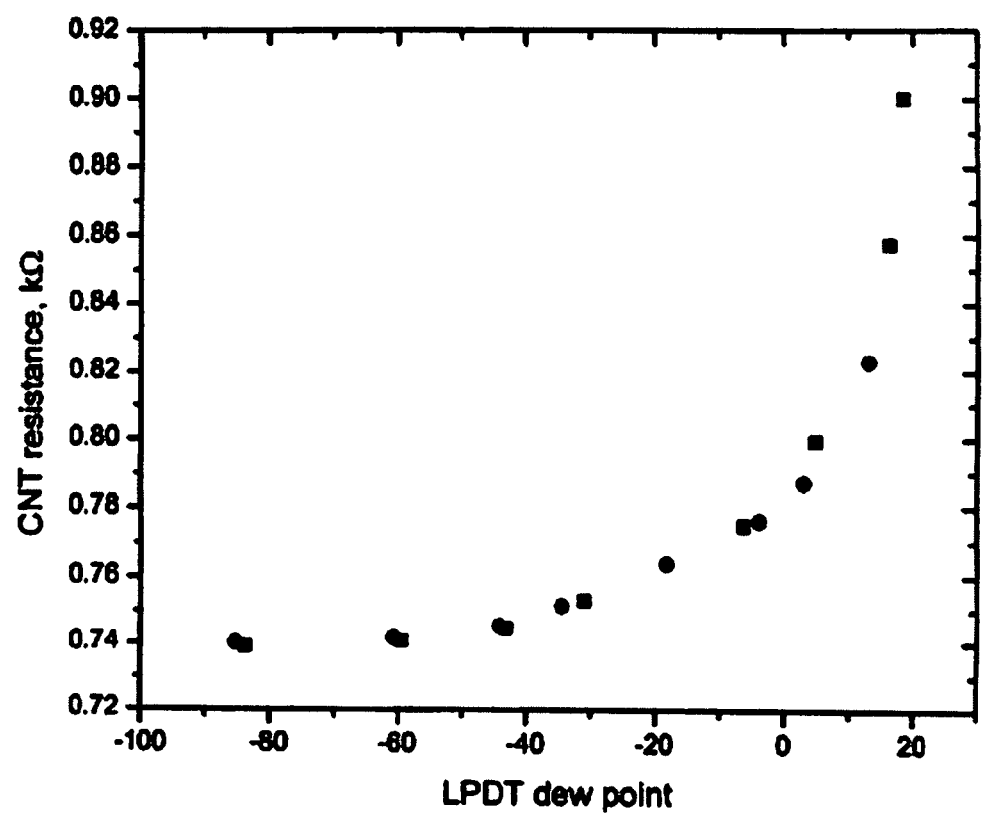
FIG. 3 shows an accelerated resistance variation of the CNT sensor of the present invention, dependent upon measured dewpoints.

The activated CNT sensor 110 is mounted between terminals 120, 130, for monitoring by signal conditioner 140 and data acquisition device 150. The signal conditioner 140 is preferably an analog to digital converter that converts an analog signal to a digital signal and outputs the converted signal to the data acquisition device 150. A current source preferably flows several μA of direct current through the activated CNT and signal conditioner 140 measures a voltage drop, which is proportional to a resistance variation of the CNT sensor 110, and provides an output to the data acquisition device 150. The resistance of the CNT sensor 110 varies according to humidity change, as monitored by the data acquisition device 150. Resistance variation of the CNT sensor 110 is provided more immediately than response times of conventional systems. The CNT sensor also provides a very high sensitivity at high dewpoint settings. As shown in FIG. 3, the CNT resistance significantly accelerates at temperatures between 5° C. and 20° C., i.e. as high dewpoint temperatures are approached.

In a preferred embodiment of the present invention, a Baseline Drift Adjuster (BDA) is provided to reset any drift from a base resistance value of the CNT that may arise from moisture accumulation within the CNT sensor or other factors during use. The BDA performs a post-heating of the CNT to remove residual moisture from the CNT sensor.

Another preferred embodiment of the BDA provides a plurality of CNTs that alternate the CNT acting as a sensor, to ensure complete drying of the CNT that is being used to perform a measurement function. Measurement is then performed as in conventional systems, such as described in the Poole '940 patent.

In other preferred embodiments of the present invention, the CNT sensor is employed as a relative humidity sensor, as an icing sensor and as a replacement for a chilled mirror type dewpoint sensor.

When employed as an icing sensor, the CNT sensor of the present invention detects icing on a molecular level, based on humidity in the air via monitoring of resistance change in the CNT. Absorption of water vapor at temperatures close to freezing conditions leads to specific non-monotonous temperature dependence of the resistance of the CNT sensor.

As the temperature decreases, intensive precipitation of the water vapor results in an increase in the resistance of CNT sensor due to the adsorption of polar water molecules with the oxidized carbon nanotubes, which are slightly negatively charged. Water molecules being adsorbed on the carbon nanotube surface create bi-layer, suppressing current flow through nanotubes is supressed by the field effect and increasing resistance.

Figure 4:
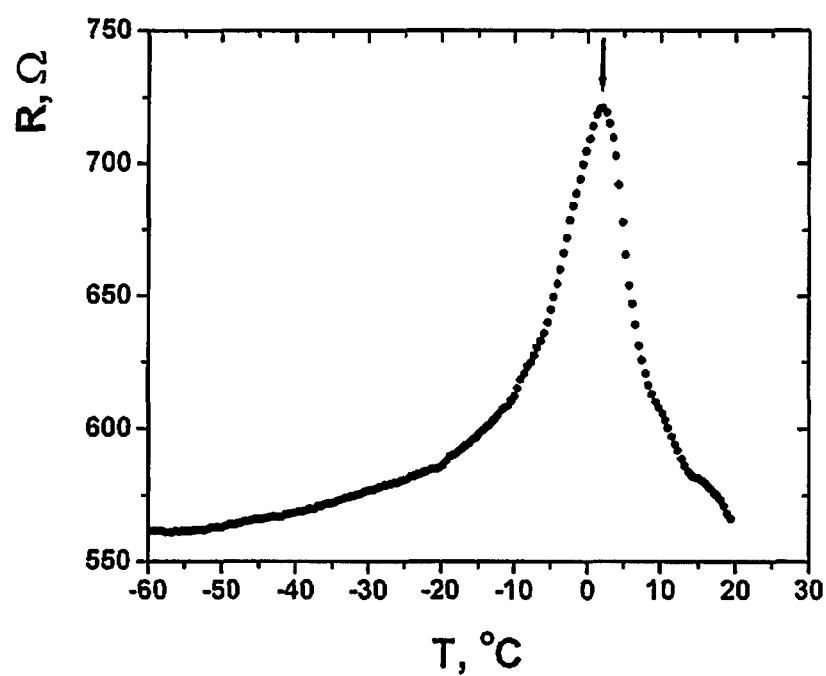
FIG. 4 is a chart showing non-monotonous temperature dependence of the resistance of the CNT sensor of the present invention.

The absorption of water vapor at temperatures close to freezing conditions leads to a specific non-monotonous temperature dependence of the resistance of the carbon CNT sensor, as shown in FIG. 4. As shown in FIG. 4, the sensor detects a dewpoint of moisture in the non-hydrocarbon gas by scanning temperature from +30° C. to −100° C., measuring resistance during the scan and determining a peak resistance.

A decrease in temperature from room temperature of approximately 20° C. to approximately a T=0° C. will result in a rapid increase of the resistance of the CNT sensor due to the water vapor condensation, reaching a maximum at the freezing point. Upon reaching the freezing point, an abrupt decrease in resistance occurs, corresponding to formation of an ice layer. The ice layer is a non-polar that surrounds the CNT surfaces and results in a sudden decrease in resistance. Since the detection occurs on a molecular level, the detection of ice formation is made without any significant ice accumulation, which is a significant improvement over conventional ice sensors.

That is, the increase in resistance of the CNT sensor is of approximately two orders of magnitude for a predetermined resistance when the surface of the CNT is wetted with water droplets. When the CNT sensor cools down, the water droplet freezes, and resistance rapidly decreases by more than one order of magnitude, thereby immediately providing an indication of ice formation. Further temperature increase results in a sudden resistance increase of approximately one order of magnitude due to the water melting. When the water dries out, the resistance of the sensor is decreasing over two orders of magnitude, to its initial value.

While the invention has been shown and described with reference to certain exemplary embodiments of the present invention thereof, it will be understood by those skilled in the art that various changes in from and details may be made therein without departing from the spirit and scope of the present invention as defined by the appended claims and equivalent thereof.

What is claimed is:

1. An apparatus for detection of a dew point of an ambient gas containing moisture and of an icing condition, the apparatus comprising:
    a sensor comprising an activated carbon nanotube (CNT) having a resistance that varies in proportion to humidity of the ambient gas;
    a signal conditioner; and
    a data acquisition device configured to monitor the resistance of the activated CNT during temperature change of the sensor to identify a peak resistance of the activated CNT positioned in the ambient gas, wherein the peak resistance of the activated CNT indicates icing of moisture in the ambient gas, and the data acquisition device further configured to identify a maximum rate of increase in said resistance verses the temperature change, which is indicative of a temperature of a dew point.

2. The apparatus of claim 1, wherein the peak resistance of the activated CNT is identified during a temperature change of the sensor from a high temperature of less than or equal to 30° C.

3. The apparatus of claim 2, wherein the peak resistance of the activated CNT is identified during a temperature change of the sensor to a low temperature of greater than or equal to −100° C.

4. The apparatus of claim 1, wherein the sensor further comprises a plurality of activated carbon nanotubes formed in one of a layer, a film, and an array.

5. The apparatus of claim 1, wherein the activated CNT changes temperature as the sensor changes temperature.

* * * * *